United States Patent
Marcincinova et al.

[11] Patent Number: 6,156,429
[45] Date of Patent: Dec. 5, 2000

[54] MONOMERS WITH DILACTONE CYCLE, AND CORRESPONDING POLYMERS

[75] Inventors: Katarina Marcincinova, Montpellier; Mahfoud Boustta, Le Cres; Jean Coudane, Lattes; Michel Vert, Castelnau-le-Lez, all of France

[73] Assignee: Centre National de la Recherche Scientifique (CNRS), Paris, France

[21] Appl. No.: 09/446,607

[22] PCT Filed: Jun. 29, 1998

[86] PCT No.: PCT/FR98/01386

§ 371 Date: Mar. 21, 2000

§ 102(e) Date: Mar. 21, 2000

[87] PCT Pub. No.: WO99/00441

PCT Pub. Date: Jan. 7, 1999

[30] Foreign Application Priority Data

Jun. 27, 1997 [FR] France ................................... 97 08145
Jun. 27, 1997 [FR] France ................................... 97 08146

[51] Int. Cl.[7] .......................... B32B 15/02; C08G 10/00
[52] U.S. Cl. ........................ 428/402; 560/179; 560/205; 568/303; 568/376; 528/220; 528/271; 528/354; 528/361; 528/370; 528/403; 528/481; 525/450; 525/471; 428/357
[58] Field of Search ..................... 560/179, 205; 568/303, 376; 528/220, 271, 354, 361, 370, 403, 481; 525/450, 471; 428/357, 402

[56] References Cited

FOREIGN PATENT DOCUMENTS 0 407 617 A1  1/1991  European Pat. Off. .
0 579 546 A2  1/1994  European Pat. Off. .

*Primary Examiner*—Samuel A. Acquah
*Attorney, Agent, or Firm*—Nixon & Vanderhye PC

[57] ABSTRACT

The invention concerns monomers with dilactonic cycle and the corresponding polymers, their preparation, and materials containing these polymers. The monomers are of formula (IIIa)

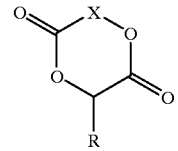

(IIIa)

in which R is the residue of an acid derived from an ose such as glyconic, gylcuronic or glycaric acid and X represents in particular a methylene or ethylene group optionally substituted by at least an alkyl, allyl, aryl or aralkyl. The corresponding polymers are in the form of degradable non-toxic products and are used for example for packaging (films) or in medicine (implants).

18 Claims, No Drawings

MONOMERS WITH DILACTONE CYCLE, AND CORRESPONDING POLYMERS

The invention relates to novel monomers with a dilactone ring and to the corresponding polymers, their preparation and the materials in which they are present.

It is known that, in the medical and surgical field, biocompatible and bioabsorbable polymers are currently being used, and also researched, for producing e.g. parts for osteosynthesis, implants capable of gradual drug release, suture threads, etc.

Biocompatible and/or biodegradable polymers are also of great value in the production of packaging products for products manufactured in industry, including the agri-foodstuffs industry, because of the ever-increasing constraints associated with environmental protection.

It is therefore important to be able to have a range of polymers which are degradable to non-toxic products and which have varied properties (especially mechanical, thermomechanical, physicochemical properties, etc.).

Novel monomers have now been discovered which afford polymers of great value in the fields which have just been mentioned.

To produce biodegradable polymers based on non-toxic products, it is desirable to use vegetable or animal raw materials of agricultural origin, which have the advantage in particular of avoiding complex chemical syntheses, when it is desired to obtain products degradable to non-toxic compounds and particularly to natural products.

Among the products of agricultural origin, oses and derivatives thereof represent an abundant and relatively inexpensive raw material. However, their use presents several problems, particularly the presence of numerous hydroxyl groups which are all capable of reacting and which therefore make it difficult to obtain definite products.

These problems can sometimes be solved by selectively protecting some of the hydroxyls in known manner, temporarily or definitively, with appropriate protecting groups. Nevertheless, the use of protecting groups is not sufficient to solve all the problems encountered. Thus, in the course of their researches, the authors of the present invention found that although δ-lactones are well known to be polymerizable, δ-gluconolactone, in which the hydroxyl groups not involved in the formation of the lactone ring are protected, only forms low molecular oligomers at best.

A novel type of monomer has now been discovered which has a dilactone ring and which, in particular, affords polymers with degrees of polymerization which, if desired, can be sufficiently high. It is thus possible to have e.g. a whole range of copolymers whose properties can easily be adjusted, especially by varying the respective proportions of the comonomers. The compound with a dilactone ring which constitutes the monomer of the invention has formula IIIa:

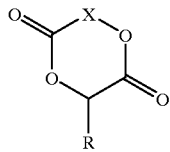

(IIIa)

in which:
R is the radical of an acid R—CHOH—CO$_2$H derived from an ose, the functional groups present in R optionally being substituted, and
X is a group —C(R$_1$)(R$_2$)— or —C(R$_1$)(R$_2$)—C(R$_3$)(R$_4$)—, in which R$_1$, R$_2$, R$_3$ and R$_4$ independently are —H or an alkyl, allyl, aryl or aralkyl group.

The invention further relates to polymers (homopolymers and copolymers) obtained from a monomer of formula III and optionally other comonomers. These polymers contain units of formula I:

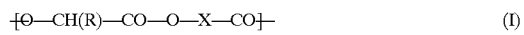

(I)

in which R and X are as defined above.

In the present patent application, the aryl groups, including those present in the aralkyl groups, are in particular optionally substituted phenyl groups, and the alkyl groups have in particular from 1 to 4 carbon atoms.

The polymers of the invention are especially linear polymers with average molecular weights which can range e.g. from 1000 to about 3 million.

The acids derived from an ose can be selected for example from those derived from an ose having from 3 to 7 carbon atoms, particularly from 4 to 6 carbon atoms, including glyceraldehyde, erythrose, threose, lyxose, xylose, arabinose, ribose, glucose, galactose and mannose, in the form of their various isomers, particularly those of the D series. The acids derived from oses are especially aldonic, uronic and aldaric acids.

Gluconic, mannonic, galactonic, ribonic, arabinonic, xylonic and erythronic acids may be mentioned in particular among the aldonic acids.

Glucuronic, galacturonic and mannuronic acids, for example, may be mentioned among the uronic acids.

Tartronic acid and tartaric, glucaric, galactaric and xylaric acids may be mentioned in particular among the aldaric acids.

As a consequence of the above:
when the acid derived from an ose is an aldonic acid, i.e. an acid of the formula

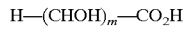

in which m is an integer which can vary in particular from 2 to 6, the monomers of formula III are especially those in which R is a group

or a corresponding group in which one or more hydroxyl groups are substituted;
when the acid derived from an ose is a uronic acid, i.e. an acid of the formula

in which p is an integer which can vary in particular from 1 to 5, the monomers of formula IIIa are especially those in which R is a group

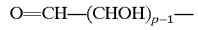

or a corresponding group in which one or more hydroxyl groups are substituted;
when the acid derived from an ose is an aldaric acid, i.e. an acid of the formula

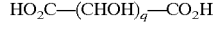

in which q is an integer which can vary in particular from 1 to 5, the monomers of formula IIIa are especially those in which R is a group of the formula

or a corresponding group in which one or more hydroxyl groups are substituted and/or in which the carboxyl group is modified, for example salified or esterified; also, when q is a number equal to at least 2, the monomer of formula IIIa can also take the form of a derivative comprising the dilactone ring at each end, as can easily be understood; in other words, in this case, R can be a group of formula VI:

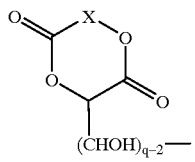

in which q is an integer which can vary for example from 2 to 5.

These last monomers of formula IIIa, comprising two dilactone rings, have the advantage of constituting not only polymerizing agents but also, by virtue of their bifunctional character, crosslinking agents, being able in particular to crosslink any polymer capable of reacting with a lactone, i.e. any polymer containing functional groups with a mobile proton, such as alcohol groups, acid groups (carboxylic acid, hemisulfate, monophosphate, diphosphate, sulfonic acid) or primary or secondary amine groups.

The methods of obtaining hydroxyl groups which are protected or more generally substituted are known.

The protection and, if appropriate, deprotection of hydroxyl groups are known and will not therefore be described in detail here; an example which may be cited is T. W. GREEN, Protective groups in Organic Synthesis, PGM Wuts, Wiley-Interscience Publications, USA (1991).

In more general terms, in the present patent application, a protected group (or functional group) denotes a group reversibly or irreversibly modified by substitution (in this sense, "protected" and "substituted" are synonymous here), it being possible for the substituent to be a protecting group in the customary sense or a group which, in addition to its protecting role (whether temporary or not), is capable of bringing valuable properties such as a pharmaceutical or cosmetological activity, a coloring ability, a fluorescent activity, plant protective properties, especially a pesticidal (e.g. insecticidal) effect, thermoreversible properties, a thermosensitive or photosensitive activity, etc. In the present patent application, the expression "protecting group" therefore denotes such substituents in general terms.

Groups capable of protecting hydroxyl groups, whether temporarily or not, are known. The following may be mentioned as examples:

ethers such as methyl, vinyl, benzyl, trityl, tetrahydrofuranyl, p-nitrobenzyl, 3,4-dimethoxybenzyl and 2-methoxyethoxymethyl ethers; or silyl ethers such as trialkylsilyl ethers, alkyldiphenylsilyl ethers and alkylphenylalkoxysilyl ethers, which can be obtained by reacting a corresponding silyl halide with an alcohol;

esters, especially sulfonates, including alkylsulfonates, phosphates, including dialkylphosphates, borates, acetates, benzoates, pivalates, sulfates, nitrates, etc.;

cyclic acetals obtained by reacting a carbonyl compound or a derivative thereof (especially acetone, benzaldehyde or formaldehyde) with two hydroxyl groups carried by two carbons located relative to one another in the α or β position on the compound carrying the hydroxyls to be protected, which gives cyclic acetals containing especially an isopropylidene, benzylidene or methylene group joining the two hydroxyls in question; for example, reaction of gluconic acid with paraformaldehyde gives a 2,4-3,5 diacetal and reaction with acetone gives a 3,4-5,6 diacetal.

A possible method of temporarily protecting the hydroxyl alpha to the carboxyl of the acid derived from the ose used as the starting material, which protection may prove necessary before carrying out the steps for protecting the other hydroxyl groups, is to form a metal complex. It is in fact known that aldonic and aldaric acids form complexes with a variety of metals (especially copper, iron, tin and barium).

By way of example, in the case of xylaric acid, the two hydroxyls alpha to the carboxyl groups can be temporarily protected by the formation of a cyclic acetal, for example with dimethoxytoluene. The remaining unprotected hydroxyl can then be protected using 2-methoxyethoxymethyl chloride to form the corresponding ether. The two alpha hydroxyls can subsequently be freed by catalytic hydrogenation.

It is pointed out that, in the case of tartaric acid, the compound of formula IIIa (where R is a group of formula VI) can be prepared without the need to protect the hydroxyls.

As indicated previously, the functional groups present in the radical R of the units of formula I are optionally substituted, for example by protecting groups as defined above.

The monomers of formula IIIa can be homopolymerized or copolymerized by the customary methods. The polymerization reactions are preferably carried out on compounds of formula III in which the hydroxyl groups, and the carboxyl group if present, are in protected form. The polymerization conditions are e.g. those described below in the particular case of copolymerization. After polymerization, the protected groups can be totally or partially deprotected and then, if desired, functionalized (especially by esterification, etherification, etc.) in order to introduce chemical groups into the polymer which are capable of imparting desired properties, for example biodegradability and/or bioabsorbability properties, solubility properties (in water or other solvents), hydrophilicity or hydrophobicity properties, mechanical strength properties, gas permeability properties, crosslinkability properties, etc.

By way of example, the apolar character of the polymers can be increased by functionalizing them with fatty chains, particularly by esterification with acylsuccinic or alkenylsuccinic anhydrides such as octenylsuccinic anhydride.

It is possible to adjust the solubility characteristics and the glass transition temperature of the polymers of the invention by crosslinking them, utilizing the reactivity of the deprotected hydroxyl groups, or by grafting the polymers onto multifunctional products such as silica or a granular starch. Crosslinking can be carried out especially with the products of formula IIIa which are derived from an aldaric acid possessing two lactone rings, as mentioned above.

The monomers and polymers of the invention can be used in a variety of fields such as agriculture, pharmacy, medicine, surgery, agrochemistry, the paper industry, packaging, etc. Depending on the particular case, the polymers of the invention can be used in these fields of application especially as rheology modifiers, sizes, suspending agents, binders, surfactants, crosslinking agents or packaging aids.

The polymers of the invention can be used especially in the fields of packaging (particularly in the form of films optionally deposited on metal foil or sheets of paper), medicine and surgery (parts for osteosynthesis, implants or microspheres for gradual drug release, suture threads), the paper industry (film-coating of paper), agriculture (mulching with film), etc.

The monomers of formula IIIa can be copolymerized with any other monomer containing groups with a mobile proton, especially:

oses or derivatives of oses, particularly derivatives of pentoses and hexoses, acids, especially diacids, of non-osidic structure, particularly those containing five or more carbon atoms, such as itaconic acid;

lactones such as poly-epsilon-caprolactone, lactide or glycolide;

polymers such as those described in European patent EP 735104, for example starches and derivatives thereof, celluloses and derivatives thereof, proteins and derivatives thereof, vinylic or acrylic polymers, etc.;

hydroxy acids HO—L—CO$_2$H capable of forming a dilactone ring or a monolactone.

The hydroxy acids HO—L—CO$_2$H capable of forming a dilactone ring are e.g. the α-hydroxy acids of the formula

HO—C(R$_5$)(R$_6$)—CO$_2$H in which R$_5$ and W independently are —H, alkyl, aryl (especially phenyl) or carboxyalkyl (especially carboxymethyl), which are capable of forming dilactones of formula IV:

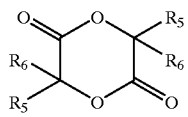

These hydroxy acids are especially those in which at least one of the substituents R$_5$ and R$_6$ is —H, for example glycolic acid or lactic, mandelic and malic acids. The units of formula II formed with these α-hydroxy acids are therefore as follows:

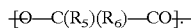

The carboxyl groups which may be present in R$_5$ and/or R$_6$ can be in free or protected form. The carboxyl groups can be protected especially in the form of esters. The hydroxy acids HO—L—CO$_2$H capable of forming a monolactone are particularly hydroxycarboxylic acids which have a hydroxyl group in the γ, δ or ε position relative to the carboxyl. Hydroxy acids capable of giving a monolactone which forms a ring having at least 6 members may be mentioned in particular.

The hydroxy acids of the formula HO—L—CO$_2$H capable of giving a lactone which forms a ring having at least six members can be selected especially from aldonic acids having at least 5 carbon atoms, such as those mentioned above, in which the hydroxyl groups not involved in the formation of the lactone can be in free or protected form.

5-Hydroxypentanoic, 2,3,4-trimethoxy-5-hydroxypentanoic and 6-hydroxy-hexanoic acids, inter alia, may also be mentioned among the hydroxy acids capable of forming a lactone ring having at least 6 members.

The invention relates in particular to a copolymer containing:

from 1 to 99%, by number of units based on the total number of units, of units of formula I:

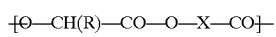 (I)

in which:

R is the radical of an acid R—CHOH—CO$_2$H derived from an ose, the functional groups present in R optionally being substituted, and X is a group —C(R$_1$)(R$_2$)— or —C(R$_1$)(R$_2$)—C(R$_3$)(R$_4$)—, in which R$_1$, R$_2$, R$_3$ and R$_4$ independently are —H or an alkyl, allyl, aryl or aralkyl group, and at least 1%, by number of units based on the total number of units, of units of formula II:

 (II)

in which:

L is the radical of a hydroxy acid HO—L—CO$_2$H selected from hydroxy acids capable of forming a dilactone ring or a monolactone.

Copolymers which contain at least 5% of units of formula II, especially those which contain from 5 to 95% of units of formula II, may be mentioned in particular among the copolymers of the invention.

The homopolymers and copolymers of the invention can be converted especially to various materials or finished articles such as powders, microspheres, films, moldings, extrudates, etc., which can be prepared by the customary techniques.

The invention further relates to a process for the preparation of a monomer or a polymer as defined above, wherein:

an acid

R'—CHOH—CO$_2$H in which R' is the radical of an acid derived from an ose, the hydroxyl groups which may be present in R' being protected, is reacted with an acid chloride of the formula

Y—X—CO—Z in which X is as defined in claim 1 and Y and Z independently are a halogen, to give a product of formula V:

 (V)

which is converted to a compound of formula III:

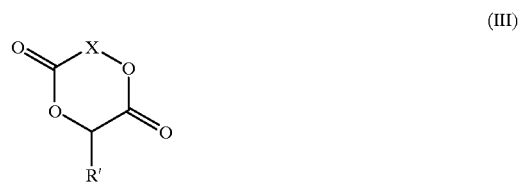 (III)

by intramolecular cyclization;

if desired, said compound of formula III is polymerized by homo-polymerization or by copolymerization with a comonomer;

if desired, at least some of the hydroxyl groups of R' are deprotected and/or functionalized; and if desired, the copolymer obtained is converted to a powder, microspheres, a film, a molding or an extrudate.

The invention relates in particular to a process for the preparation of a copolymer or a material or finished article as defined above. The invention relates especially to a process wherein:

a) at least one monomer of formula III:

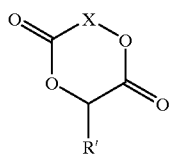

(III)

in which:
R' is the radical of an acid R'—CHOH—CO$_2$H derived from an ose, in which the hydroxyl groups which may be present in R' are protected, and X, R$_1$, R$_2$, R$_3$ and R$_4$ are as defined above,
and at least one monomer selected from dilactones and monolactones derived from a hydroxy acid HO—L—CO$_2$H as defined above,
are reacted under conditions which allow copolymerization;
b) if desired, at least some of the hydroxyl groups of R' are deprotected and/or functionalized; and
c) if desired, the copolymer obtained is converted to a powder, micro-spheres, a film, a molding or an extrudate.

The copolymerization process of the invention therefore consists in reacting a compound of formula III as defined above: a) with a compound of formula IV such as e.g. glycolide or D—, L— or DL-lactide, and/or b) with a monolactone, particularly a monolactone which forms a ring having at least 6 members, especially a lactone of an aldonic acid having 5 or 6 carbon atoms (for example δ-gluconolactone), δ-valerolactone or ε-caprolactone.

The copolymerization of the compounds of formula III with the compounds of formula IV or the monolactones can be carried out either in bulk or in solution in a solvent, generally in the presence of an appropriate catalyst or initiator.

The reaction temperature and time depend especially on the reactants employed and the desired average molecular weight of the copolymer prepared. These parameters can easily be determined by simple routine experiments. The reaction is generally carried out at a temperature of 20 to 200° C., under an inert atmosphere or in a sealed reactor, for a time which can range e.g. from a few minutes to 30 days.

The initiators or catalysts used in the copolymerization reaction are of a type known for this kind of reaction, tin octanoate, tetraphenyltin, powdered metallic zinc, zinc lactate, alkoxyaluminum compounds and lanthanide or yttrium derivatives may be mentioned in particular.

The polymer obtained can be purified by the customary methods.

It is possible to deprotect all or some of the protected groups of the copolymer obtained and/or to functionalize the deprotected or unprotected groups. The functionalization consists in particular in substituting said deprotected or unprotected groups with other protecting groups as defined above.

The functionalization enables the copolymers to acquire particular properties, especially pharmaceutical properties (using a substituent derived from a drug), physical properties (for example thermal or solubility properties) and physicochemical properties (for example hydrophilicity or hydrophobicity properties), or a particular chemical reactivity, including biodegradability and/or bioabsorbability properties. Functionalization with bifunctional reagents also makes it possible to carry out crosslinking reactions. For example, dicarboxylic derivatives, such as itaconic acid, allow crosslinking by reaction with hydroxyl groups of the polymer, and polyols (for example oses or polyethylene glycols) allow crosslinking by reaction with previously activated carboxyl groups of the polymer.

The starting material of formula III can be prepared by reacting an acid R'—CHOH—CO$_2$H, as defined above, with an acid chloride of the formula

Y—X—CO—Z in which X is as defined above, Y is a halogen, particularly chlorine or, preferably, bromine, and Z is a halogen, particularly bromine or, preferably, chlorine.

This gives a product of formula V:

Y—X—CO—O—CH(R')—CO$_2$H     (V)

which is converted to a compound of formula III by intramolecular cyclization with the elimination of hydrohalic acid YH.

The copolymers of the invention can be random copolymers or block copolymers of the type A—B, A—B—A or B—A—B, A being e.g. a polymerization product composed of units of formula I and B a polymerization product composed of units derived from the comonomer used, for example units of formula II. It is easy to understand that block polymers can be obtained especially in the case where the polymerization of the compound of formula III is started before the comonomer, for example the monolactone or dilactone, is added.

By varying the respective proportions of the units derived from III and the units derived from the comonomer, especially the units derived from IV (or the units derived from the monolactone), it is possible to adjust the properties of the copolymer. For example, when the compound III is a gluconic acid derivative and the compound IV is lactide, it has been found that the glass transition temperature of the copolymer increases, relative to the glass transition temperature of polylactic acid, when the proportion of the units derived from the compound III increases (cf. experimental section below).

The Examples which follow illustrate the invention.

EXAMPLES

The following abbreviations and symbols are used in the experimental section below:

| | |
|---|---|
| m.p. | melting point |
| Tg | glass transition temperature |
| DMF | dimethylformamide |
| ether | ethyl ether |
| PLA50 | poly(D,L-lactide) |
| δ-gluconolactone | δ-D-gluconotactone |
| gluconic acid | D-gluconic acid |

Example 1

Preparation of DIPAGYL (monomer derived from gluconic acid)

A. Preparation of methyl 3,4-5,6-diisopropylidenegluconate (MDIPAG)

20 g of δ-gluconolactone, 34 cm$^3$ of 2,2-dimethoxypropane, 20 cm$^3$ of acetone, 6 cm$^3$ of methanol and 0.24 g of p-toluenesulfonic acid are mixed. The heterogeneous mixture obtained is stirred at room temperature for 48 h and becomes homogeneous during the reaction.

The solvents are evaporated off under reduced pressure at 30° C. The residue is dissolved in ether and washed with water. The organic phase is dried over magnesium sulfate and the solvent is then evaporated off.

The product obtained is in the form of a colorless viscous oil which is insoluble in water and hexane and soluble in organic solvents such as ether, toluene, tetrahydrofuran, chloroform, acetone, dioxane and DMF.

$[\alpha]_D = -1.8°$ cm$^2$g$^{-1}$(589 nm, dioxane).

The IR spectrum and $^1$H and $^{13}$C NMR spectra are consistent with the indicated structure.

B. Preparation of 3,4-5,6-diisopropylidenegluconic acid (DIPAG)

29.3 g of MDIPAG are dissolved in 80 cm$^3$ of 1 M aqueous NaOH solution. The solution is heated at 80° C. for 10 min, with stirring. It is then cooled to 0° C. and the pH is adjusted to 2 by adding 2 M aqueous hydrochloric acid solution cooled to 0° C. Extraction is carried out with dichloromethane. The organic phase obtained is dried over magnesium sulfate, filtered and evaporated under reduced pressure.

This gives a white powder which is soluble in organic solvents such as ether, toluene, tetrahydrofuran, chloroform, acetone, dioxane and DMF, and soluble in water at basic pH. The product reprecipitates at acid pH. It is insoluble in hydrocarbon solvents.

M.p.=154° C.

$[\alpha]_D = -1.6°$ cm$^2$g$^{-1}$(589 nm, dioxane).

C. Preparation of 2-bromoacetyl-3,4-5,6-diisopropylidenegluconic acid (BDIPAG)

25.1 g of DIPAG are dissolved in 300 cm$^3$ of ethyl ether under a nitrogen atmosphere. 8 cm$^3$ of bromoacetyl chloride are added over 30 min at room temperature, with stirring. After a reaction time of 15 min, the solution is cooled to between 0 and 5° C. and 15 cm$^3$ of triethylamine are added without the temperature exceeding 5° C. The mixture is stirred for 4 hours at 5° C. 450 cm$^3$ of ether are then added. The organic phase is washed with aqueous hydrochloric acid solution, dried over magnesium sulfate and filtered and the solvent is then evaporated off.

This gives a product in the form of an oil which is soluble in ether, toluene, tetrahydrofuran, chloroform, acetone, dioxane, DMF and methanol, insoluble in water and partially soluble in hexane and cyclohexane (hot). The product is sensitive to hydrolysis and is stored in the freezer.

$[\alpha]_D = +14.1°$ cm$^2$g$^{-1}$(589 nm, dioxane).

The IR spectrum and $^1$H and $^{13}$C NMR spectra are consistent with the indicated structure.

D. Preparation of 3-(1,2-3,4-tetraoxobutyldiisopropylidene)-1,4-dioxane-2,5-dione (DIPAGYL)

31.8 g of BDIPAG are dissolved in 100 cm$^3$ of DMF. The solution obtained is added over 5 hours at 40° C., with vigorous stirring, to a mixture comprising 11.4 g of NaHCO$_3$ and 1.1 liters of DMF and stirring is then continued for 4 hours after the addition has ended. The solvent is evaporated off under reduced pressure and the residue is extracted with ether. The extract is washed with water and dried over magnesium sulfate and the solvent is then evaporated off under reduced pressure. The residue is purified by chromatography on a silica column using a 4:1 (v:v) dichloromethane/heptane mixture as the eluent.

The fractions containing the expected product are combined and the solvents are evaporated off. The residue is recrystallized from a 3:1 (v:v) cyclohexane/heptane mixture.

The product can be purified by sublimation at 85° C. under reduced pressure (0.1 Pa). This gives white crystals (m.p.=87° C.), which are stored under an inert atmosphere (argon).

The IR and $^1$H NMR spectra are consistent with the indicated structure.

The product is soluble in ether, toluene, tetrahydrofuran, chloroform, acetone, dioxane, DMF and methanol, as well as in cyclohexane (hot).

$[\alpha]_D = -29.2°$ cm$^2$g$^{-1}$(589 nm, dioxane).

Analogously, replacing the bromoacetyl chloride with 2-bromopropionyl chloride in step C) above gives a compound of formula III, derived from gluconic acid, in which X is —CH(CH$_3$)—.

Example 2

Preparation of 3-(1,2-dioxoethylisopropylidene)dioxane-2,5-dione a) The starting material used is an aqueous solution containing erythronic acid in equilibrium with erythronolactone. This aqueous solution contains 29.4% by weight of erythronic acid and 30.4% by weight of erythronolactone. 20 grams of this solution are evaporated under reduced pressure at 60° C. to give a white powder, which is redissolved in methanol and precipitated with ether. The precipitate is filtered off and dried under reduced pressure to give 9.5 g of erythronolactone, which are solubilized in 50 cm$^3$ of methanol to which 50 mg of p-toluenesulfonic acid have been added. The solution is refluxed for three hours. The opening of the lactone ring and the formation of the methyl ester can be followed by infrared spectrometry. After a reaction time of three hours, no change is observed. The reaction medium is cooled and 30 ml of 2,2-dimethoxypropane are added. The mixture is stirred for 24 hours at 20° C., after which 1.5 g of OH$^-$ ion exchange resin are added. After a reaction time of two minutes, the mixture is filtered and the solvent is evaporated off to give methyl 3,4-isopropylideneerythronate.

b) 8.7 g of this product are dissolved in 45 cm$^3$ of 1.2 M sodium hydroxide solution. After stirring for ten minutes, the solution is cooled to 0° C. and 1 M aqueous hydrochloric acid solution cooled to 0° C. is added until the pH is 7. The solution is concentrated by evaporation down to a volume of 20 cm$^3$ and is cooled to 0° C. Sodium chloride is added in a sufficient amount to give a saturated solution. The pH of the solution is adjusted to 2 by adding 1 M hydrochloric acid solution cooled to 0° C., and extraction is carried out with one liter of dichloromethane cooled to 0° C. The organic phase is dried, filtered and evaporated to give 3,4-isopropylideneerythronic acid. The infrared spectrum is consistent with the indicated structure.

c) 3.2 g of 3,4-isopropylideneerythronic acid are dissolved in 60 cm$^3$ of dichloromethane. 1.9 cm$^3$ of bromoacetyl chloride are added under a nitrogen atmosphere, with stirring. The mixture is cooled to 0° C. and 4.2 cm$^3$ of triethylamine are added dropwise without the temperature exceeding 5° C. The mixture is stirred for three hours and then extracted with dichloromethane. The extract is washed with water and dried over magnesium sulfate. It is filtered and the solvent is evaporated off to give the 2-bromoacetate of 3,4-isopropylidene-erythronic acid.

d) 4.2 g of this product are dissolved in dimethylformamide. This solution is added to a mixture of 1.9 g of $NaHCO_3$ and 100 $cm^3$ of dimethylformamide, with stirring, and stirring is then continued for 4 hours. The solvent is evaporated off and the residue is extracted with ether and washed with water. The ether is evaporated off. The product obtained is purified by chromatography on a silica column using a 9:1 (v:v) dichloromethane/heptane mixture as the eluent. The fractions containing the expected product are combined and the solvents are evaporated off The residue is recrystallized from cyclohexane. The 3-(1,2-dioxoethylisopropylidene)dioxane-2,5-dione obtained is a solid melting at 92° C. It can be purified by sublimation at 80° C. under reduced pressure ($10^{-3}$ mm of mercury, i.e. 0.13 Pa). The IR and $^1H$ NMR spectra are consistent with the indicated structure.

Replacing the bromoacetyl chloride with 2-bromopropionyl chloride in step c) above gives a compound of formula III, derived from erythronic acid, in which X is —$CH(CH_3)$—.

Example 3

Homopolymerization of 3-(1,2-3,4-tetraoxobutyldiisopropylidene)-1,4-dioxane-2,5-dione (DIPAGYL)

1 g of DIPAGYL is introduced into a Carius tube. The monomer is brought to the molten state and degassed by means of successive vacuum-nitrogen cycles. The initiator is then introduced under a nitrogen atmosphere. The tube is sealed under vacuum for the bulk polymerization experiments. The tubes are placed at 110° C. for 7 days, with shaking. The experimental conditions are collated in Table 1.

TABLE 1

Conditions of polymerization of 3-(1,2-3,4-tetraoxobutyldiisopropylidene)-1,4-dioxane-2,5-dione

| Experiment no. | INITIATOR | [I]/[M]* (molar) | Type of polymerization |
| --- | --- | --- | --- |
| 1 | Zinc lactate | 1/300 | Cationic |
| 2 | $SbF_3$ | 1/300 | Cationic |
| 3 | Tin octanoate | 1/300 | Cationic |
| 4 | Potassium acetate | 1/300 | Anionic |

*[I/M] = molar ratio Initiator/Monomer (DIPAGYL)

The products obtained at the end of the polymerization reaction have different appearances.

To determine the molecular weight of the products obtained, analyses were performed by size exclusion chromatography (SEC) in an organic medium of dioxane.

To isolate the fractions of different molecular weights, sample 1 was purified by dissolution in dioxane and precipitation in ethanol.

The results of the molecular weight analysis by SEC after purification are collated in Table 2.

TABLE 2

Molecular weights of the products obtained by the polymerization of DIPAGYL, after purification

| Experiment no. | MOLECULAR WEIGHT | YIELD (%) | COLORATION |
| --- | --- | --- | --- |
| 1 | 3200 | 40 | Light brown |
| 2 | 19,700 | 91 | Light brown |
| 3 | 19,900 | 73 | Light brown |
| 4 | 5400 | 90 | Dark brown |

Example 4

Copolymerization of 3-(1,2-3,4-tetraoxobutyldiisopropylidene)-1,4-dioxane-2,5-dione (DIPAGYL) with D,L-lactide The copolymerization of DIPAGYL with D,L-lactide produces a family of copolymers of the polyester type whose physicochemical and mechanical properties can be adjusted via the proportion of starting comonomers.

DIPAGYL and D,L-lactide are placed in a round-bottomed flask and degassed by performing 3 cycles comprising evacuation ($10^{-3}$ mbar) at 90° C. followed by the passage of a stream of argon in the cold. The initiator (tin octanoate) is then added. The molar ratio initiator/comonomers is 1/600. The flask is sealed under reduced pressure and placed in an oil bath. It is rotated about an inclined axis during the copolymerization reaction, which is carried out for 5 days under vacuum at a temperature of 120° C. When the reaction has ended, the reaction mixture is left to cool and ambient pressure is re-established. The reaction mixture is dissolved in acetone. The solution is filtered to remove the insoluble fraction, and the copolymer is reprecipitated in methanol to give a crude copolymer, which can be purified by size exclusion chromatography. Three copolymers were synthesized starting from a mixture of monomers respectively containing 50 mol %, 30 mol % and 15 mol % of DIPAGYL. The results are summarized in the Table below:

| Copolymer | % DIPAGYL[1] in the copolymers | MW[2] | Ip[3] |
| --- | --- | --- | --- |
| Copolymer 1 | 47 | 68,000 | 2.5 |
| Copolymer 2 | 31 | 115,000 | 2.1 |
| Copolymer 3 | 13 | 103,500 | 2.8 |

[1] mol % evaluated by NMR
[2] weight-average molecular weight (product obtained before precipitation in methanol)
[3] polymolecularity index (1) mol % evaluated by NMR
(2) weight-average molecular weight (product obtained before precipitation in methanol)
(3) polymolecularity index The yields of the copolymerization are around 90%.

The $^1H$ and $^{13}C$ NMR spectra are consistent with the indicated structure.

The copolymers obtained are amorphous. The incorporation of DIPAGYL, units into PLA causes a considerable variation in the glass transition temperature, which increases with the proportion of DIPAGYL in the copolymers, as shown in the Table below:

| Product | Tg (° C.) |
|---|---|
| Copolymer 1 | 83 |
| Copolymer 2 | 73 |
| Copolymer 3 | 65 |
| PLA50 | 56 |

The DIPAGYL/D,L-lactide copolymers are film-forming and moldable polymers. Films can be obtained especially by evaporating a solution of the copolymer in a solvent such as acetone or dioxane.

Moldings can be obtained for example under the following molding conditions:

preheating of the mold at 150° C. for 30 min, deposition of the polymer in powder form, heating for 3 min without applying pressure, molding with pressure increase (5 MPa/min) up to 20 MPa, termination of compression and cooling to room temperature.

Example 5

Deprotection of the alcohol groups

The DIPAGYL/D,L-lactide copolymers obtained in Example 4 contain alcohol groups protected by acetal protecting groups. The corresponding polyhydroxylated polymers can be obtained by removal of the protecting groups in an acid medium.

For example, 1 g of copolymer 3 obtained in Example 4 is dissolved in 10 cm³ of dichloromethane. 1.5 cm³ of water and 10 cm³ of trifluoroacetic acid are added at 5° C. The mixture is stirred for 5 min and 100 cm³ of ether are then added. The polyhydroxylated polymer precipitates. It is separated off by decantation and dried under reduced pressure.

The degree of deprotection of the alcohol groups, determined by $^1$H NMR, is of the order of 50%.

The weight-average molecular weight of the partially deprotected copolymer represents about 75% of that of the starting copolymer.

Example 6

Preparation of a compound of formula III derived from xylaric acid

Dimethoxytoluene and methanol are reacted with xylaric acid in the presence of p-toluenesulfonic acid. After stirring for three days at room temperature, the solvents are evaporated off in the cold under reduced pressure. Methyl 2,4-benzylidenexylarate is obtained after purification.

The product obtained is dissolved in chloroform, and 2.4 equivalents of diisopropylethylamine are added at 0° C. under a nitrogen atmosphere. After a reaction time of ten minutes, methoxyethoxymethyl chloride is added under the same conditions. The mixture is heated at 60° C. for fourteen hours. It is cooled to room temperature and extracted with dichloromethane. The extract is washed with very dilute aqueous hydrochloric acid solution and then with water. The organic phase is dried and the solvent is evaporated off to give methyl 3-methoxyethoxy-methyl-2,4-benzylidenexylarate.

By following a procedure analogous to that described in step B of Example 1, the diethyl ester is hydrolyzed to the corresponding dicarboxylic acid.

The 2,4-benzylidene group is then removed by hydrogenation in the presence of palladium deposited on active charcoal to give the 3-methoxyethoxy-methyl ether of xylaric acid.

By following procedures analogous to those described in steps C and D of Example 1, the corresponding xylaric acid derivative is obtained; this contains the ring shown in formula III (where X is —CH$_2$—) at each end, these two rings being joined by the group

—CH(O—CH$_2$—O—C$_2$H$_4$—OCH$_3$)—.

What is claimed is:

1. Monomers of the formula:

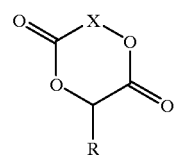

in which:

R is the radical of an acid R—CHOH—CO$_2$H derived from an ose, the functional groups present in R optionally being substituted, and X is a group —C(R$_1$)(R$_2$)— or —C(R$_1$)(R$_2$)—C(R$_3$)(R$_4$)—, in which R$_1$, R$_2$, R$_3$ and R$_4$ independently are —H or an alkyl, allyl, aryl or aralkyl group, or polymers obtained starting from at least one of said monomers, comprising units of formula I:

$$\text{—}[\text{O}\text{—CH(R)}\text{—CO}\text{—O}\text{—X}\text{—CO}]\text{—} \quad (I)$$

in which R and X are as defined above.

2. Monomer or polymer according to claim 1 in which said ose contains from 3 to 7 carbon atoms.

3. Monomer or polymer according to claim 1 in which said acid derived from an ose is selected from the group consisting of aldonic, uronic and aldaric acids.

4. Monomer or polymer according to claim 1 in which said acid derived from an ose is an aldonic acid.

5. Polymer resulting from the polymerization of at least one monomer as defined in claim 1.

6. Copolymer resulting from the polymerization of at least one monomer as defined in claim 1 and at least one comonomer.

7. Copolymer according to claim 6 in which said comonomer contains groups with a mobile proton.

8. Copolymer according to claim 7 containing units of formula II:

$$\text{—}[\text{O}\text{—L}\text{—CO}]\text{—} \quad (II)$$

in which:

L is the radical of a hydroxy acid HO—L—CO$_2$H selected from hydroxy acids capable of forming a dilactone ring or a monolactone.

9. Copolymers according to claim 8 containing from 1 to 99%, by number of units based on the total number of units, of units of formula I and at least 1%, by number of units based on the total number of units, of units of formula II.

10. Copolymer according to claim 9 containing at least 5% of units of formula II.

11. Copolymer according to claim 8 in which said unit of formula II is a unit $$\text{—}[\text{O}\text{—C(R}_5\text{)(R}_6\text{)}\text{—CO}]\text{—}$$

in which $R_5$ and $R_6$ independently are —H or an alkyl, aryl or carboxyalkyl group.

12. Copolymer according to claim 11 in which said unit of formula II is derived from an acid HO—L—$CO_2H$ capable of forming a monolactone whose lactone ring has at least 6 members.

13. Copolymer according to the preceding claim in which said unit of formula II is derived from an acid HO—L—$CO_2H$ selected from aldonic acids, 5-hydroxypentanoic acid and 6-hydroxyhexanoic acid.

14. Material or finished article containing a homopolymer or a copolymer as defined in claim 1, said material taking the form of a powder, microspheres, a film, a molding or an extrudate.

15. Process for the preparation of a monomer or a polymer as defined in claim 1, wherein:

an acid

R'—CHOH—$CO_2H$ in which R' is the radical of an acid derived from an ose, the hydroxyl groups which may be present in R' being protected, is reacted with an acid chloride of the formula

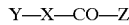

Y—X—CO—Z in which X is as defined in claim 1 and Y and Z independently are a halogen, to give a product of formula V:

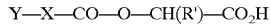

Y—X—CO—O—CH(R')—$CO_2H$  (V)

which is converted to a compound of formula III:

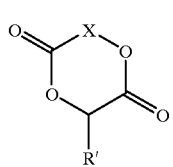

(III)

by intramolecular cyclization;
if desired, said compound of formula III is polymerized by homopolymerization or by copolymerization with a comonomer;
if desired, at least some of the hydroxyl groups of R' are deprotected and/or functionalized; and
if desired, the copolymer obtained is converted to a powder, microspheres, a film, a molding or an extrudate.

16. Process according to claim 15 wherein the comonomer is selected from the group consisting of dilactones and monolactones derived from a hydroxy acid as defined in claim 8.

17. Process according to claim 16 wherein said dilactone has the formula

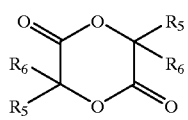

in which $R_5$ and $R_6$ independently are —H or an alkyl, aryl or carboxyalkyl group.

18. Process according to claim 17 wherein said dilactone is selected from glycolide and D—, L— or DL-lactide.

* * * * *